United States Patent [19]
Bryan et al.

[11] Patent Number: 5,661,243
[45] Date of Patent: Aug. 26, 1997

[54] SHEET MATERIAL DETECTOR

[75] Inventors: Michael Bryan, Watford Herts; Roger Arthur Whitney, Stanmore; Malcolm Hatfield Avery, Ruislip Middlesex, all of England

[73] Assignee: Eastman Kodak Company, Rochester, N.Y.

[21] Appl. No.: 615,059

[22] Filed: Mar. 13, 1996

[30]   Foreign Application Priority Data

Apr. 28, 1995 [GB] United Kingdom ............... 9508654

[51] Int. Cl.⁶ ..................... G01N 29/08; G01N 29/24
[52] U.S. Cl. ................. 73/632; 73/159; 73/597; 73/598; 73/599; 73/600
[58] Field of Search ................ 73/597, 598, 599, 73/600, 159, 632, 644, 642; 364/550; 340/675

[56]   References Cited

U.S. PATENT DOCUMENTS

| | | |
|---|---|---|
| 3,918,704 | 11/1975 | Sugiyama et al. |
| 4,519,249 | 5/1985 | Hunt .................... 73/159 |
| 4,545,248 | 10/1985 | Kitada et al. .......... 73/597 |
| 4,594,897 | 6/1986 | Bantz .................... 73/600 |
| 4,612,807 | 9/1986 | Wunderer ............. 73/580 |
| 4,901,577 | 2/1990 | Roberts ................. 73/60 |
| 5,488,867 | 2/1996 | Dorr ..................... 73/597 |

FOREIGN PATENT DOCUMENTS

| | | |
|---|---|---|
| 710124 | 6/1954 | United Kingdom. |
| 1124898 | 8/1968 | United Kingdom. |
| 1290978 | 9/1972 | United Kingdom. |
| 2 128 330 | 4/1984 | United Kingdom. |

Primary Examiner—Hezron E. Williams
Assistant Examiner—Nashmiya Ashraf
Attorney, Agent, or Firm—Clyde E. Bailey, Sr.

[57]   ABSTRACT

A sheet material detector has an ultrasonic transmitter and an ultrasonic receiver spaced from one another to permit the passage of a sheet of material therebetween in use. The transmitter and the receiver are mounted on a support to transmit and receive the ultrasonic beam respectively along an axis which is at an acute angle, preferably in the range from 50° to 70°, in relation to the plane of the sheet material in use, and each of the transmitter and the receiver includes a hood for shielding the ultrasonic beam against contamination by stray sound waves reflected from extraneous bodies or at the surface of the web or sheet. The detector also includes output signal responsive to the received ultrasonic beam for generating an output signal. One application of the detector is in splice detecting apparatus for detecting the presence of splices in a web of material, and another application is in edge detecting apparatus for indicating the position of an edge of the web or sheet of material.

8 Claims, 7 Drawing Sheets

SHEET MATERIAL DETECTOR

FIELD OF THE INVENTION

The present invention concerns a sheet material detector. In the context of the present specification, the expression "sheet material" covers both continuous web material and individual sheets of material.

BACKGROUND OF THE INVENTION

The use of sensors is well-known in the manufacture and handling of sheet material, for guiding the material through the various stages of a processing plant. For example, sensors may be employed to detect the edges of a web for generating an edge position signal for use in controlling the position of the web in relation to individual work stations. Alternatively, sensors may be employed for detecting the presence of a splice in a web for generating a splice indication output for activating apparatus at a selected work station, eg. for cutting the web.

PROBLEM TO BE SOLVED BY THE INVENTION

Particular problems arise in relation to the manufacture and handling of light sensitive material, such as photographic film and paper, for a number of reasons. Firstly, the light sensitive emulsions are very easily scratched and damaged, and as a result the handling of such material has to be largely by non contacting techniques. Secondly, the use of non contacting sensors of the optical variety is prohibited by the light sensitivity of the material.

Ultrasonic sensors have been known for a number of years but their use in the manufacture and handling of light sensitive materials has hitherto been problematic in situations where a precision output is required because such sensors are highly sensitive to signals from extraneous sources. Their outputs are regularly affected by mechanical shocks or by reflections from extraneous surfaces or by reflections by the sheet material itself due to web flap, and it has not hitherto been possible to employ them in precision handling situations.

Consequently, there has long been a need for an accurate sensor or detector for use in the manufacture and handling of light sensitive materials in, for example, the photographic industry. Such a sensor or detector would, of course, also find application in many other fields.

SUMMARY OF THE INVENTION

The present invention provides a sheet material detector comprising an ultrasonic transmitter and an ultrasonic receiver spaced from one another to permit the passage of sheet material therebetween, means for supporting the transmitter and the receiver respectively to transmit and receive the ultrasonic beam along an axis directed at an acute angle to the plane of the sheet material in use, a shield for protecting the ultrasonic beam from the effects of stray sound waves, and output signal means responsive to the received ultrasonic beam for generating a control output.

Preferably, the axis of the ultrasonic beam is arranged to be at an angle in the range from 50° to 700° in relation to the plane of the sheet material in use, and in the preferred embodiment described below this angle is approximately 60°.

Advantageously, the shield is in the form of a respective hood for each of the transmitter and the receiver, both for limiting the spread of the ultrasonic beam for preventing the reflection of stray sound waves from extraneous surfaces and for absorbing stray sound waves caused by reflection at the surface of the sheet material.

Each hood may be formed from foam rubber material and may also include at least one lead wall. Further, each hood preferably terminates in a surface lying parallel to the plane of the sheet material in use.

ADVANTAGEOUS EFFECT OF THE INVENTION

In this way, the hoods define a narrow path for the ultrasonic beam and protect the beam against the reflection of sound waves from extraneous bodies and from sound waves reflected at the surface of the sheet material. This is particularly important because the generation of standing waves between the transmitter and the receiver is prevented, and as a result the detector is largely immune to false signals produced by web flap.

In one application, the detector is employed in splice detecting apparatus for generating a splice indication output indicative of the presence of a splice in the sheet material.

In another application, the detector is employed in edge detecting apparatus for generating an edge position signal representing the position of an edge of the sheet material.

BRIEF DESCRIPTION OF THE DRAWINGS

The invention is described further, by way of example, with reference to the accompanying drawings, in which.

DETAILED DESCRIPTION OF THE INVENTION

Figure 1:
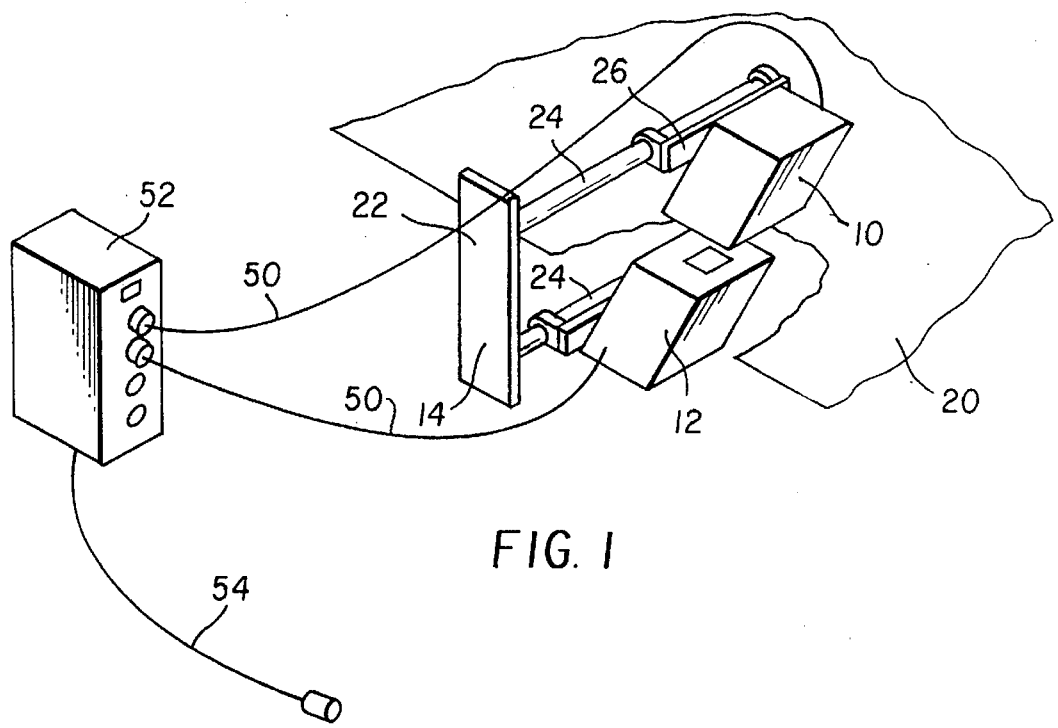
FIG. 1 is a perspective view of a web or sheet detector embodying the present invention.
Figure 2:
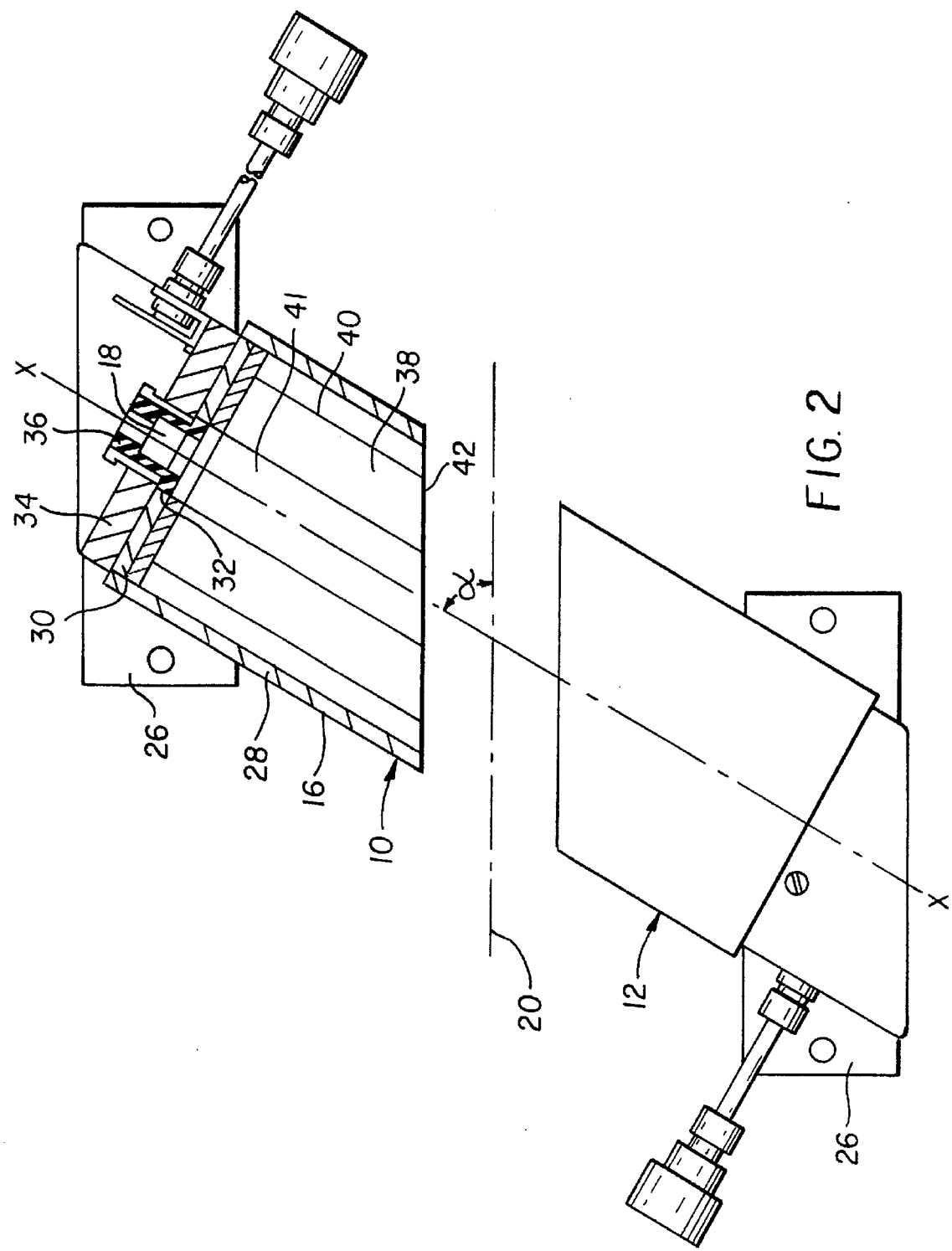
FIG. 2 is a section through transmitting and receiving heads of the detector shown in FIG. 1.

Referring initially to FIGS. 1 and 2, a web detector according to the apparatus comprises an ultrasonic transmitter 10 and an ultrasonic receiver 12 mounted on a support 14. Each of the transmitter 10 and the receiver 12 comprises a head 16 carrying an ultrasonic transducer 18, and the heads 16 are spaced from one another to allow a web 20 of material to pass therebetween in use without contacting either of the heads 16.

The arrangement of the support 14 and the heads 16 ensures that the ultrasonic beam between the transducer 18 travels along an axis X—X which lies at an acute angle α relative to the plane of the web 20 in use. As a result, sound waves reflected from the surface of the web 20 are directed away from the path of the ultrasonic beam and out of the region where they might affect the level of energy transmitted between the ultrasonic transducers 18. In the present instance, the angle α is approximately 60°, which is considered the optimum for the reduction of standing waves between the ultrasonic transducers 18. However, it will be appreciated that other angles may be used so long as the axis of the ultrasonic beam is not nearly perpendicular to the web. The best results are expected with an angle in the range from 50° to 70°.

In order to achieve this desired arrangement of the heads 16 and the transducer 18, the support 14 comprises a bracket 22 provided with a pair of arms 24, which are located parallel to one another. Each arm 24 has a mounting plate 26 fixed thereto and, as shown, the mounting plates 26 are fixed at different distances along the arms 24 to provide a respective mount for the associated head 16. The heads 16 are attached to the mounting plates 26 to face one another along the axis X—X.

The construction of both of the heads 16 is the same, and therefore only one will be described with reference to FIG. 2. As shown, the head 16 comprises a rigid square housing 28 closed at its relatively outer end by a wall 30 formed with a central opening 32. The ultrasonic transducer 18 is mounted over the opening 32 by way of a carrier plate 34 secured to the wall 30 and a silicon rubber mount 36 carried by the carrier plate 34. The silicon rubber mount 36 serves to absorb mechanical shock and vibrations, which might otherwise affect the output of the ultrasonic transducer 18.

The interior of the rigid housing 28 contains a sound absorbing foam lining 38 filling the interior of the housing 28 apart from a narrow passage 41 along the axis X—X providing a path for the ultrasonic beam. Embedded in the lining 38 is a thin lead wall 40 as shown. The housing 28, together with the lining 38 and the lead wall 40, all terminate in a surface 42, which is disposed parallel to the plane of the web. The function of the foam 38 and the lead wall 40 is firstly to limit the spread of the ultrasonic beam by absorbing sound waves which stray beyond the narrow passage 41 to prevent such sound waves bouncing off extraneous objects and causing interference. Further, the form of the housing 28, and lining 38 terminating in the surface 42 will ensure that sound waves from the ultrasonic beam reflected from the surface of the web 20 will gradually be absorbed by the foam lining 38 as they bounce to and fro and will be attenuated. Conversely, of course, sound waves from outside the detector reflected from the surface of the web 20 towards the ultrasonic beam will also be absorbed by the foam lining 38. Finally, waves impinging on the exterior of the housing 28 towards the ultrasonic beam will also be absorbed by the foam lining 38.

The ultrasonic beam is thus substantially protected against interference and only sound waves passing along the axis X—X and transmitted across the web 20 will contribute to web detection and any eventual measurement. This is particularly important because it means that web flap, which is a relatively common occurrence in a moving web, may cause reflections in the transmitted sound waves but will not affect the reading because waves set up by such flap are reflected away from the beam and gradually absorbed.

The two ultrasonic transducers 18 are connected by means of electrical leads 50 to a control box 52, which is itself connected by a further lead 54 to a power supply (not shown). The control box contains circuitry (described in greater detail below) for generating a 40 kHz sinusoidal signal for driving a piezo-ceramic crystal in the transducer 18 in the ultrasonic transmitter. In use, the ultrasonic beam thus produced impinges on and passes through the web 20 and is attenuated by an amount proportional to the density of the web in the region underneath the transmitter 10. The attenuated beam is sensed by the ultrasonic transducer 18 in the receiver 12, which supplies an electrical output signal representative of the received ultrasonic beam. This output signal is processed by signal processing circuitry in the control box 52 to provide a control output.

Figure 3:
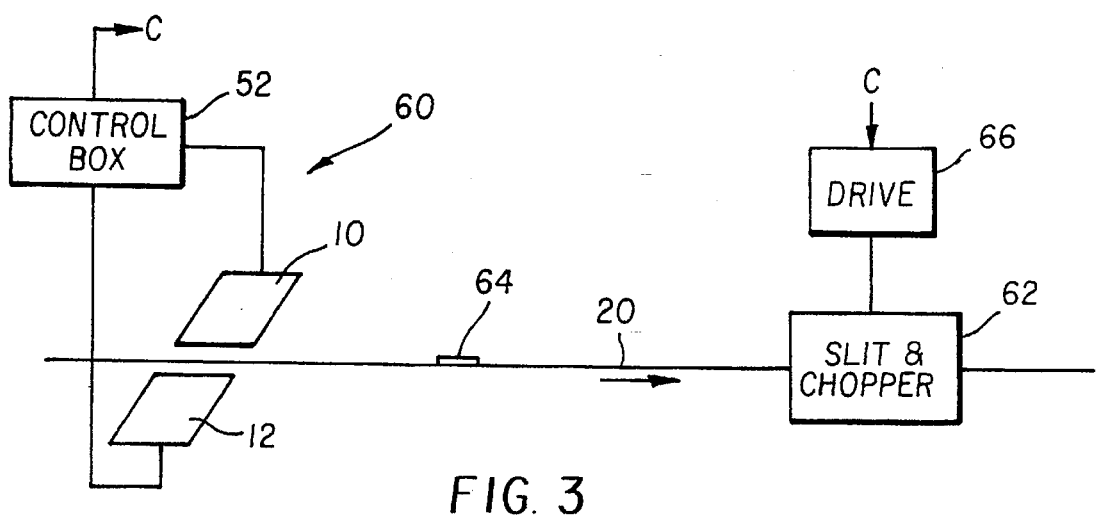
FIG. 3 is a diagrammatic view illustrating an application of the detector in splice detecting apparatus.
Figure 4:
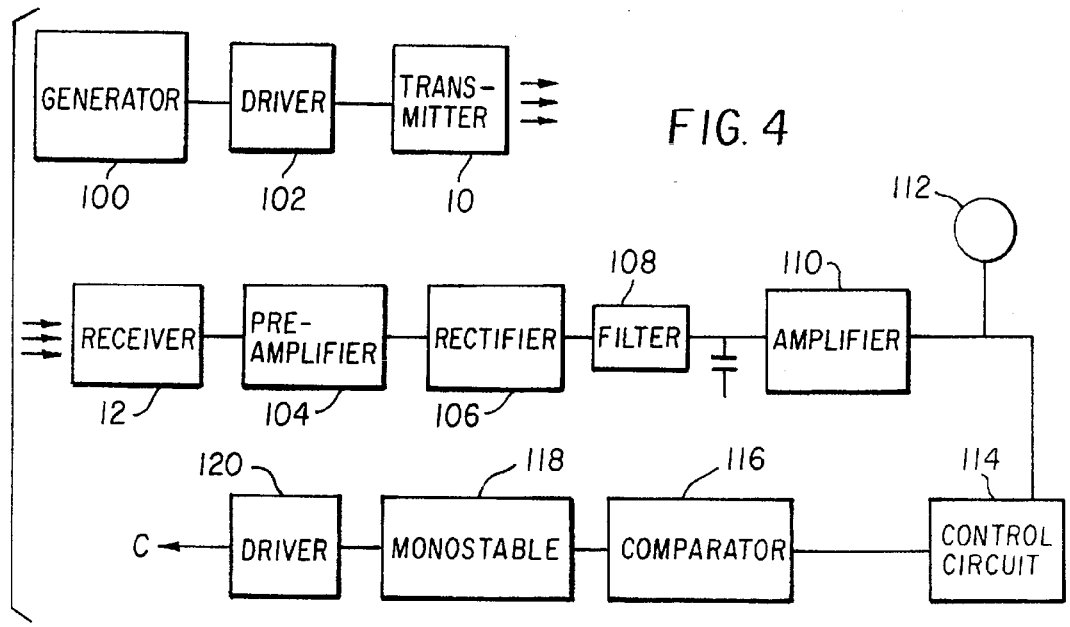
FIG. 4 is a circuit diagram of the circuitry employed in the splice detecting apparatus.

One application of the web detector as a splice detector is illustrated in FIG. 3, and the circuitry in the control box 52 in this instance is illustrated in FIG. 4.

Referring first to FIG. 3, the web 20 is arranged first to pass through a splice detector 60, which is arranged approximately in the middle of the web 20 in the lateral direction or at least substantially inset from the web edges. Downstream of the splice detector 60, the web 20 passes through a slit and chopping apparatus 62, which cuts the web 20 both laterally and longitudinally to form individual sheets of material. In order to minimise waste when a splice 64 occurs in the web 20, the slit and chopping apparatus is arranged to cut the web 20 laterally immediately upstream and immediately downstream of the splice 64 and to discard the row of sheets including the splice 64. The integrity of all the remaining sheets is then unimpaired by blemishes due to the splice 64.

For this purpose, the splice detector 60 is arranged to detect the presence of the splice 64, and the control box 52 of the splice detector 60 is arranged to generate a control output C after an appropriate delay for application to a drive 66. The drive 66 responds to the control output C by appropriate control of the cutter in the slit and chopping apparatus 62 to make slits on either side of the splice 64 and then discard this region of the original web 20.

FIG. 4 shows the circuitry employed for generating the control output C, and FIG. 5 is a signal diagram showing the signals at different stages of such circuitry.

Figure 5A:
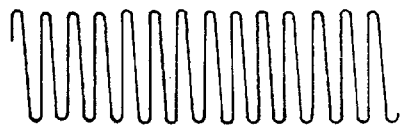
FIG. 5 is a signal diagram showing the signals at various stages of the circuitry of FIG. 4.

As shown in FIG. 4, a wave form generator 100 in the form of an oscillator produces a 40 kHz sinusoidal waveform, which is shown in FIG. 5a. This waveform is supplied to a driver 102 which activates a piezo-ceramic crystal constituting the transducer 18 in the ultrasonic transmitter 10.

Figure 5B:
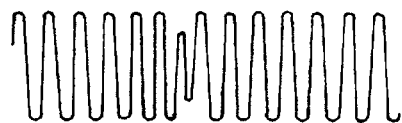
Figure 5C:
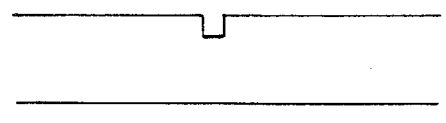

The transmitted ultrasonic beam passes through the web 20 and is attenuated thereby by an amount dependent on the mass per unit length of the web 20 and is received by the transducer 18 in the ultrasonic receiver 12. When a splice occurs, the attenuation of the transmitted signal increases temporarily so that there is a corresponding reduction in the signal output by the receiver 12. This signal, after amplification in a preamplifier 104 is shown in FIG. 5b. The output from the preamplifier 104 is supplied through a halfwave rectifier 106 and a filter 108 to an amplifier 110 to produce the signal shown in FIG. 5c which is a single rectangular pulse. A meter 112 monitors the level of the base signal.

The output from the amplifier 110 is supplied by way of an automatic gain control circuit 114 to a comparator 116. The automatic gain control circuit monitors the amplitude of the base signal over a relatively long time period by comparison with the duration of the pulse shown in FIG. C, and is thereby unaffected by the presence of the pulse. In the event that the signal level of the base signal changes due to a change in web material, then the automatic gain control circuit 114 makes a gain adjustment to bring the base signal to a predetermined level at its output. Consequently, the output of the automatic gain control circuit 114 is a base signal having a constant predetermined level, which is interrupted by a brief rectangular pulse whenever a splice occurs.

Figure 5D:

This output is supplied to the comparator 116 where it is compared with a reference signal. The output of the comparator 116 goes high whenever a rectangular pulse is detected and is supplied by way of a monostable 118 providing a delay to a driver 120. The output from the comparator 116 is illustrated in FIG. 5d.

Figure 5E:

The driver 120 supplies the control output C, which is selectively in the form of a voltage pulse shown in FIG. 5e or in the form of a relay activation signal as required.

In this application, the circuitry is required merely to generate an indication of the presence of the splice 72, for example in the form of the voltage pulse. It is not required to produce a measurement signal because the splice 72 is formed by butting two edges of web material and applying a tape of standard width and thickness to bridge the join, and so the thickness variation of the web at the splice is already known. In an alternative form of splice detector, of course, the signal processing circuitry could be adapted to provide a measurement signal indicative of the thickness of the splice and/or the width of the splice.

Figure 6:
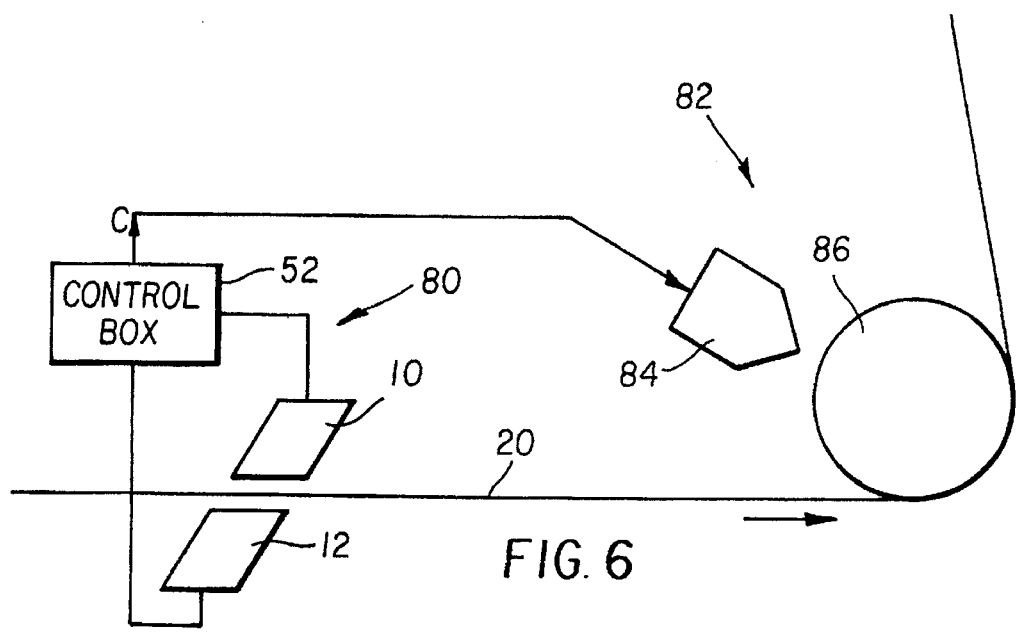
FIG. 6 is a diagrammatic view illustrating an application of the detector in edge detecting apparatus.
Figure 7:
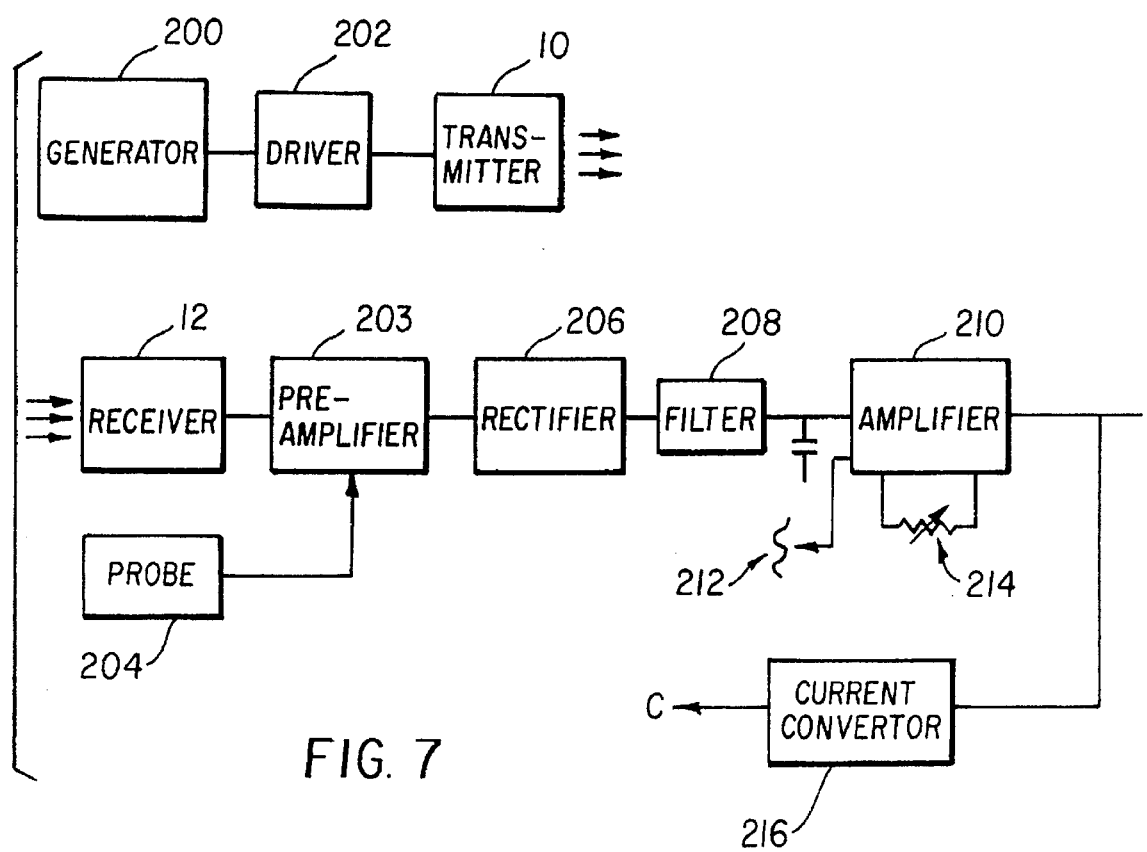
FIG. 7 is a circuit diagram of the circuitry employed in the edge detecting apparatus.

An application of the detector as an edge position detector 80 is illustrated in FIG. 6 with the signal processing circuitry employed in this instance in the control box 52 being shown in FIG. 7.

FIG. 6 differs from FIG. 3 in that the edge position detector 80 is situated adjacent an edge of the web 20 to detect and measure variations in the position of this edge and generate a corresponding control output C. The control output C is then applied to a steering frame 82 located for steering the web 20 and controlling its lateral position generally or through a subsequent work station. For this purpose, the edge detector 80 applies the control output C to a control arm 84 of the steering frame 82 which in turn adjusts a steering roller 86 as necessary to reposition the web laterally to correct any wander. Other edge position detectors 80 and associated steering frames 82 will also be situated at intervals along the path of the web. Indeed edge position detectors 80 may also be employed alone for monitoring the position of the edge of the web for other reasons for example to detect the alignment of the web following a join.

Turning to FIGS. 7 and 8, the signal processing circuitry for this application and the corresponding signals will now be described.

Figure 8A:
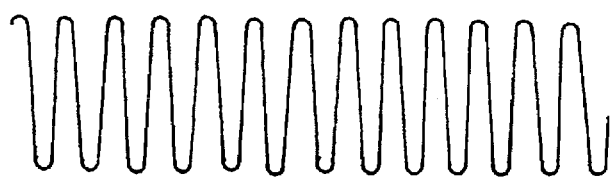
FIG. 8 is a signal diagram of the signals at various stages in the circuitry of FIG. 7.
Figure 8B:
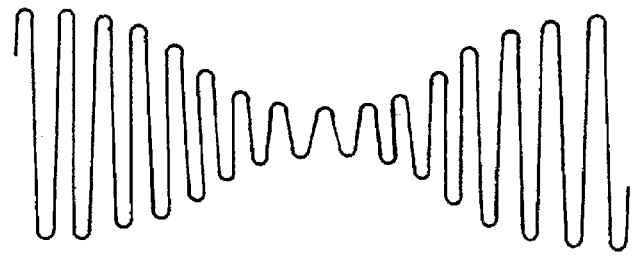

A wave form generator in the form of an oscillator 200 generates a 40 kHz sinusoidal signal as before, which is shown in FIG. 8a, and a driver 202 is responsive to this signal to drive the piezo-ceramic crystal constituting the transducer 18 of the ultrasonic transmitter 10. The ultrasonic beam is transmitted past the edge of the web 20 and is attenuated by an amount which is dependent on the degree to which the edge of the web 20 covers or obstructs a part of the beam. The attenuated beam is picked up by the transducer 18 in the ultrasonic receiver 12 and supplied to a preamplifier 203. The received signal, however, is affected not only by the position of the edge of the web 20 but also by the ambient temperature, and in order to compensate for this a temperature probe 204 measures the ambient temperature and supplies a temperature signal to the preamplifier 203 to control the gain of this amplifier. The output of the amplifier 203 is illustrated in FIG. 8b and show how the envelope of the received signal varies continuously with variations in the position of the edge of the web 20.

Figure 8C:
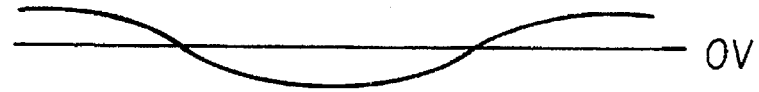

The output from the preamplifier 203 is supplied by way of a halfwave rectifier 206 and a filter 208 to an amplifier 210. The amplifier 210 also has an offset control input 212 and a gain control input 214 and is precalibrated such that a web neutral position corresponding with the edge of the web 20 covering one half of the area of the transmitted ultrasonic beam is represented by an output from the amplifier 210 of 0 volts. The overall output from the amplifier 210 is illustrated in FIG. 8C and it will be seen that this is a continuously varying signal, which crosses the 0 volt axis on each occasion that the edge of the web 20 passes through the neutral position.

The voltage output from the amplifier 210 is supplied to a voltage to current convertor 216 to supply a control output in the form of a current, since this is the form of output required to drive the steering frame 82.

Although the above description has been confined to the use of the invention in relation to web detection, and particularly the detection of a splice in a web or the detection of the edge position of a web, the invention can equally well be applied to the detection of individual sheets, for example to the detection of spaces between sheets or an edge position of each sheet.

A further application of the detector as a gap detector for detecting the spaces between individual sheets of material will now be described with reference to FIGS. 9 to 11.

Figure 9:
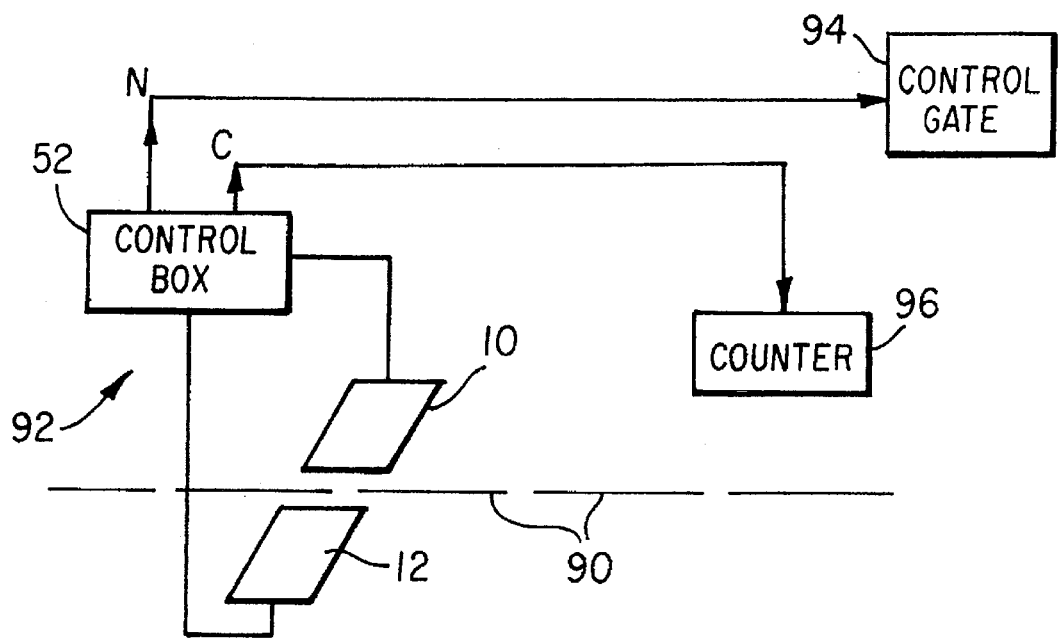
FIG. 9 is a diagrammatic view illustrating an application of the detector in a sheet gap detecting apparatus.

Referring to FIG. 9, individual sheets of material 90 are arranged to pass through the gap detector 92, which is arranged approximately in the middle of the path of the sheets 90. The gap detector 92 detects firstly the presence of splices in the individual sheets and generates a corresponding control output C as in the case of the apparatus shown in FIG. 4, and secondly the presence of each gap between the individual sheets and generates a further output N in the form of a corresponding pulse. The output C is applied to a control gate 94 of a packing machine for causing the gate to discard sheets including a splice, and the output N may for example be applied to a counter 96 for counting the sheets being packed.

Figure 10:
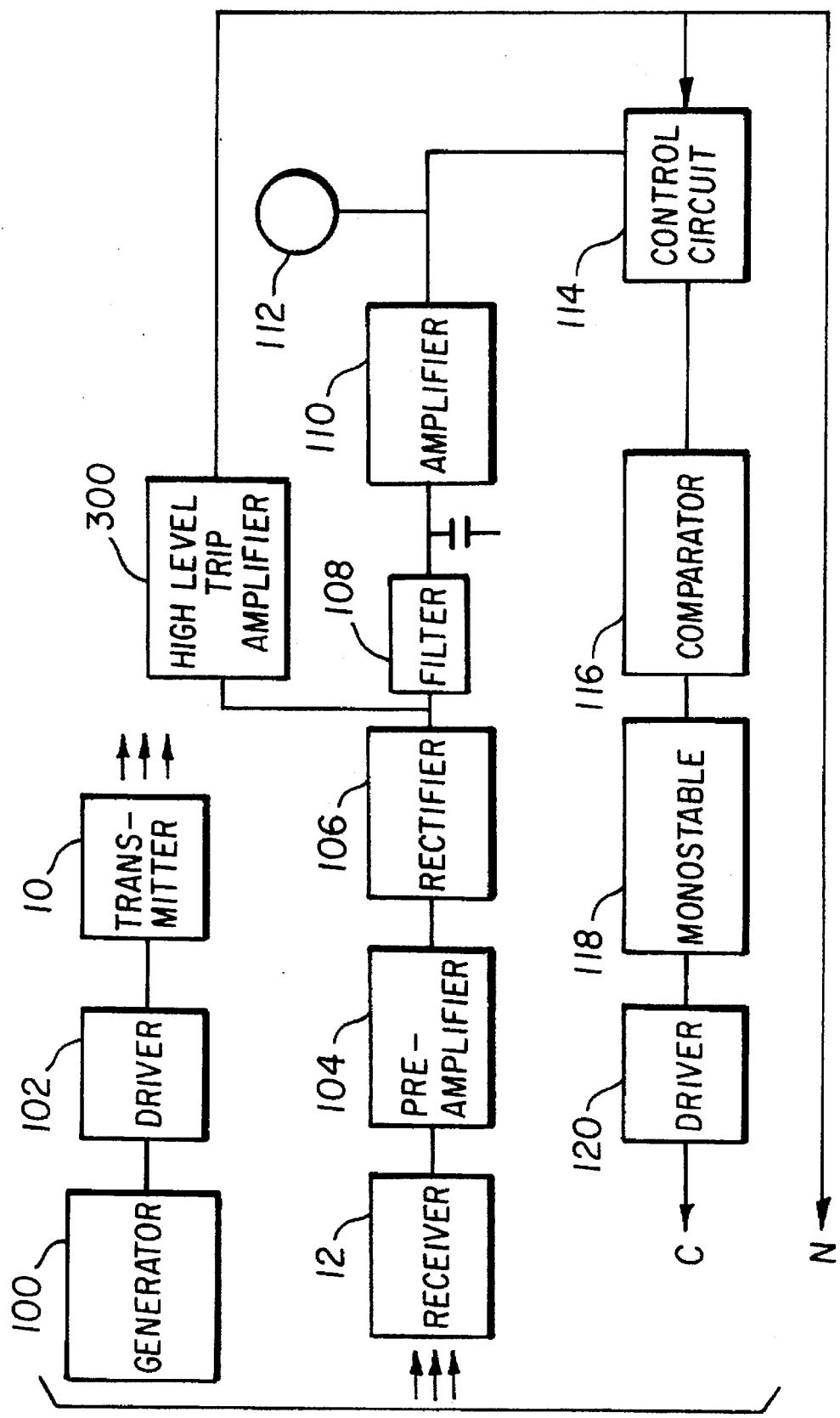
FIG. 10 is a circuit diagram of the circuitry employed in the sheet gap detecting apparatus.

FIG. 10 shows the circuitry employed for generating the control outputs C and N in this instance, and FIG. 11 is a signal diagram showing the signals at certain stages of the circuitry. The circuitry shown in FIG. 10 is in many respects similar to the circuitry of FIG. 4 employed in the splice detecting apparatus and like parts are designated by the same reference numerals and will not be described in detail. Likewise, the signals occurring in the FIG. 10 circuitry and corresponding to those shown in FIG. 5 are omitted in FIG. 11 and will not be described.

Figure 11A:
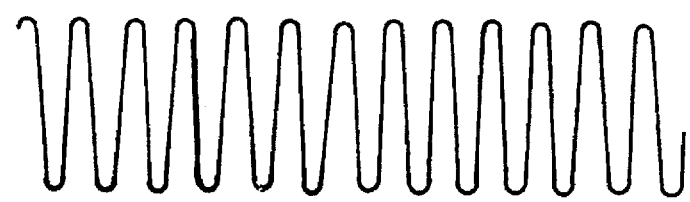
FIG. 11 is a signal diagram of the signals at various stages in the circuitry of FIG. 10.

As shown in FIG. 10, the wave form generator 100 produces the 40 kHz sinusoidal wave form, which is shown in FIG. 11a and which is supplied to the driver 102 for driving a piezo-ceramic crystal constituting the transducer 18 in the ultrasonic transmitter 10.

Figure 11B:
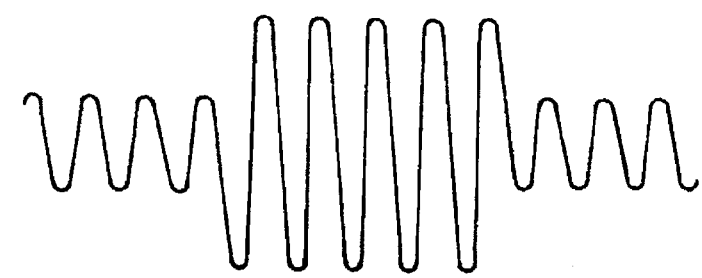
Figure 11C:

The transmitted ultrasonic beam passes through the sheets 90 and is attenuated thereby and is received by the transducer 18 in the ultrasonic receiver 12. When a splice occurs, this is detected as described above and the control output C is produced. When a gap occurs, there is temporarily no attenuation and the signal output by the receiver 12 increases correspondingly. This signal, after amplification in the preamplifier 104 is shown in FIG. 11b. The output from the amplifier 104 is supplied by way of the halfwave rectifier 106 and filter 108 to the amplifier 110 to produce the signal shown in FIG. 11c, which is a single rectangular pulse of large and undefined amplitude. This undefined pulse is supplied to the automatic gain control circuit 114 and, in the absence of appropriate measures, would upset the normal functioning of the circuit 114 for detecting changes in the material of the individual sheets.

Figure 11D:

Therefore, in order to prevent the circuit 114 from reacting incorrectly to a gap between the sheets, a clamp and blank signal of known amplitude shown in FIG. 11d is derived from the output of the halfwave rectifier 106 by way of a high level trip amplifier 300. This clamp and blank signal is applied to the automatic gain control circuit 114 to cause the circuit 114 to blank out the unwanted part of the input constituting the undefined pulse and to hold its output in the condition it was in immediately preceding the arrival of the undefined pulse. Consequently, the automatic gain control circuit 114 is enabled to monitor the amplitude of the base signal and make a suitable gain adjustment when changes in the material of the individual sheets are detected, but without being affected by the change in signal level produced by gaps between the sheets.

The rectangular pulses generated by the high level trip amplifier 300 in response to such gaps in addition to being supplied to the automatic gain control circuit 114 are also supplied as the further output N as shown and may be used for counting the ambers of sheets to be packed.

We claim:

1. A sheet material detector comprising an ultrasonic transmitter for transmitting an ultrasonic beam and an ultrasonic receiver for receiving said ultrasonic beam, said ultrasonic transmitter and said ultrasonic receiver being spaced from one another to permit the passage of sheet material therebetween, means for supporting the transmitter and the receiver respectively to transmit and receive the ultrasonic beam along an axis directed at an acute angle to the plane of the sheet material in use, a shield defining a beam passageway along said axis, said beam passageway comprising an innermost shock absorbing foam layer and an outermost lead layer embedded in said innermost shock absorbing foam layer for protecting the ultrasonic beam from the effects of stray sound waves, said shield further comprising a first hood constituting a part of the ultrasonic transmitter and a second hood constituting part of the ultrasonic receiver, and wherein each of said first and second hoods has a face arranged parallel to the plane of the sheet material in use, and output signal means responsive to the received ultrasonic beam for generating an output signal.

2. A detector according to claim 1 in which the axis of the ultrasonic beam is in the range from 500° to 70° relative to the plane of the sheet material in use.

3. A detector according to claim 2 in which the axis of the ultrasonic beam is at 60° relative to the plane of the sheet material in use.

4. A detector according to claim 1 in which the shield is arranged to limit the spread of the ultrasonic beam for preventing the reflection of sound waves from extraneous surfaces.

5. A detector according to claim 1 in which the shield is arranged to absorb stray sound waves caused by reflection at the surface of the sheet material.

6. Splice detecting apparatus comprising a sheet material detector according to claim 1, and signal processing means responsive to the output signal for generating a splice indication output indicative of the presence of a splice in the sheet material.

7. Edge detecting apparatus comprising a sheet material detector according to claim 1, and signal processing means responsive to the output signal for generating an edge position signal representing the position of an edge of the sheet material.

8. Gap detecting apparatus comprising a sheet material detector according to claim 1, and signal processing means responsive to the output signal for generating a gap signal indicative of the presence of a gap between sheets of the sheet material.

* * * * *